(12) United States Patent
Kakehi et al.

(10) Patent No.: US 7,575,901 B2
(45) Date of Patent: Aug. 18, 2009

(54) METHOD FOR PRODUCING NUCLEOTIDE BY FERMENTATION

(75) Inventors: Masahiro Kakehi, Kawasaki (JP); Yoshihiro Usuda, Kawasaki (JP); Yukiko Tabira, Kawasaki (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 811 days.

(21) Appl. No.: 10/798,339

(22) Filed: Mar. 12, 2004

(65) Prior Publication Data
US 2004/0152171 A1 Aug. 5, 2004

Related U.S. Application Data

(62) Division of application No. 09/891,287, filed on Jun. 27, 2001, now abandoned.

(30) Foreign Application Priority Data
Jul. 5, 2000 (JP) .............................. 2000-204260

(51) Int. Cl.
*C12P 19/38* (2006.01)
(52) U.S. Cl. .................... 435/87; 435/196; 435/252.33; 536/23.2
(58) Field of Classification Search ................. 435/87, 435/196, 252.33; 536/23.2
See application file for complete search history.

(56) References Cited

FOREIGN PATENT DOCUMENTS

| EP | 1 004 663 | 5/2000 |
|---|---|---|
| JP | 40-24515 | 10/1965 |
| JP | 54-20195 | 2/1979 |
| JP | 56-12438 | 3/1981 |

OTHER PUBLICATIONS

Tso et al. (Apr. 10, 1982) J. Biol. Chem., vol. 257, No. 7, pp. 3525-3531 (GenBank accession J01666).*
Tiedeman et al. (Jul. 25, 1985) J. Biol. Chem., vol. 260, No. 15, pp. 8676-8679.*
GenBank (Apr. 26, 1993) accession M10101.*
H. Momose, et al., J. Gen. Appl. Microbiol., vol. 10, No. 4, pp. 343-358, 1967, "Genetic and Biochemical Studies on 5'-Nucleotide Fermation".
M. Fujimoto, et al., Agr. Biol. Chem., vol. 29, No. 10, pp. 918-922, 1965, "Studies on 5'-Nucleotidase-Lacking Mutants Derived from *Bacillus subtilis*".
A. Furuya, et al., Applied Microbiology, vol. 16, No. 7, pp. 981-987, Jul. 1968, "Production of Nucleic Acid-Related Substances by Fermentative Processes".
H. Neu, The Journal of Biological Chemistry, vol. 242, No. 17, pp. 3896-3904, Sep. 10, 1967, "The 5'-Nucleotidase of *Escherichia coli*".
A. Cowman, et al., Gene, vol. 12, pp. 281-286, 1980, "Molecular Cloning of the Gene (*ush*) From *Escherichia coli* Specifying Periplasmic UDP-Sugar Hydrolase (5'Nucleotidase)".
M. C. Thaller, et al., FEMS Microbiology Letters, 146, pp. 191-198, 1997, "Identification of the Gene (*aphA*) Encoding the Class B Acid Phosphatse/Phosphotransferase of *Escherichia coli* MG1655 and Characterization of its Product".
F.R. Blattner, Science 277, vol. 5331, GenBank Accession No. AAC77025, pp. 1453-1474, 1997, "The Complete Genome Sequence of *Escherichia coli* K-12".
H. Tao, Journal of Bacteriology, vol. 181, No. 20, pp. 6425-6440, Oct. 1999, "Functional Genomics: Expression Analysis of *Escherichia coli* Growing on Minimal and Rich Media".
M.W Laird, Abstracts pf the General Meeting of the American Society, XP-001042299, vol. 100, pp. 435-436, May 21-25, 2000, "Essential Role of the AphA Periplasmic Acid Phosphatase in Utilization of 5'-Nucleotides by *Escherichia coli purEK ushA phoA* Mutants".
G.M. Rossolini, et al., CMLS Cellular and Molecular Life Sciences, XP-001024401, vol. 54, No. 8, pp. 833-850, 1998, "Bacterial Non-specific Acid Phosphohydrolases: Physiology, Evolution and Use As Tools in Microbial Biotechnology".
H. Matsui, et al., Agric. Biol. Chem., XP-001073798, vol. 46, No. 9, pp. 2347-2352, 1982, "5'Nucleotidase Activity in Improved Inosine-Producing Mutants of *Bacillus subtilis*".
H. Nielsen, et al., Protein Engineering, XP-002200196, vol. 10, No. 1, pp. 1-6, 1997, "Identification of Prokaryotic and Eukaryotic Signal Peptides and Prediction of Their Cleavage Sites".

* cited by examiner

*Primary Examiner*—Tekchand Saidha
(74) *Attorney, Agent, or Firm*—Oblon, Spivak, McClelland, Maier & Neustadt, P.C.

(57) ABSTRACT

Nucleoside 5'-phosphate ester is produced by culturing a bacterium belonging to the genus *Escherichia* having an ability to produce nucleoside 5'-phosphate ester, in which ushA gene and aphA gene do not function normally, in a medium to produce and accumulate nucleoside 5'-phosphate ester in the medium, and collecting the nucleoside 5'-phosphate ester from the medium.

5 Claims, No Drawings

METHOD FOR PRODUCING NUCLEOTIDE BY FERMENTATION

This application is a Divisional of U.S. application Ser. No. 09/891,287, filed on Jun. 27, 2001, now abandoned.

BACKGROUND OF THE INVENTION

1. Field of the Invention

The present invention relates to a method for producing nucleotides by fermentation. Nucleotides such as nucleoside 5'-phosphate esters are useful as seasonings, drugs, raw materials thereof and so forth.

2. Description of the Related Art

As methods for industrial production of nucleoside 5'-phosphate esters, there are known methods comprising producing nucleoside by fermentation and enzymatically phosphorylating the obtained nucleoside to obtain nucleoside 5'-phosphate ester.

On the other hand, methods of directly producing nucleoside 5'-phosphate esters by fermentation have also been proposed. For example, Japanese Patent Publication (Kokoku) No. 56-12438 discloses a method for producing 5'-guanylic acid, which comprises culturing a mutant strain of a bacterium belonging to the genus *Bacillus* showing adenine auxotrophy and resistance to decoyinine or methionine sulfoxide and having an ability to produce 5'-guanylic acid (guanosine 5'-monophosphate, also abbreviated as "GMP" hereinafter) and collecting GMP produced and accumulated in the medium. Further, there are several reports on deriving strains which produce 5'-inosinic acid (inosine 5'-monophosphate, also abbreviated as "IMP" hereinafter) from inosine producing strains of *Bacillus subtilis* (Magasanik, B. et al., *J. Biol. Chem.*, 226, 339 (1957); Fujimoto, M., et al., *Agr. Biol. Chem.*, 30, 605 (1966)). However, the production of nucleoside 5'-phosphate esters by direct fermentation generally suffers from insufficient yield, and it is not so practical compared with the aforementioned enzymatic methods.

As the reasons for the difficulty of IMP production by direct fermentation, there are mentioned bad cell permeability of IMP and quite ubiquitous distribution of degradative enzymes that decompose IMP (Nucleic Acid Fermentation, Edited by Aminosan Kakusan Shudankai, Kodansha Scientific, Japan). To overcome these obstacles, there has been attempted to delete nucleotide degradative activity. As degradative enzymes that decompose IMP into inosine, 5'-nucleotidase, acid phosphatase, alkaline phosphatase and so forth are conceived (Nucleic Acid Fermentation, supra). Further, the aforementioned Japanese Patent Publication No. 56-12438 also suggests that a bacterial strain showing high GMP yield can be obtained from a mutant strain showing reduced nucleotidase activity.

As a technique for producing nucleoside 5'-phosphate ester on an industrial level, a method of producing IMP by using a mutant strain of *Brevibacterium ammoniagenes* has been developed (Furuya et al., *Appl. Microbiol.*, 16, 981 (1968)).

As described above, various studies have been made on the production of nucleoside 5'-phosphate esters by direct fermentation, and some successful examples are also known. However, there are many unknown points about nucleotide degradative enzymes, and it cannot be said that improvement of yield has been studied sufficiently. In particular, no example of production of nucleoside 5'-phosphate esters on a practical level has been known for *bacteria* belonging to the genus *Escherichia*.

SUMMARY OF THE INVENTION

The present invention was accomplished in view of the technical situation described above, and an object of the invention is to provide a method for producing nucleoside 5'-phosphate ester such as IMP using a *bacterium* belonging to the genus *Escherichia*.

The inventors of the present invention assiduously studied in order to achieve the aforementioned object. As a result, they found that a gene coding for 5'-nucleotidase other than the known gene existed in *Escherichia coli*, and successfully identified the gene. Further, they found that *Escherichia coli* having inosine producing ability or guanosine producing ability became to produce IMP or GMP, if the novel gene was disrupted in addition to the known 5'-nucleotidase gene. Thus, they accomplished the present invention.

That is, the present invention provides the followings.

(1) A method for producing nucleoside 5'-phosphate ester, comprising the steps of culturing a *bacterium* belonging to the genus *Escherichia* having an ability to produce nucleoside 5'-phosphate ester, in which ushA gene and aphA gene do not function normally, in a medium to produce and accumulate nucleoside 5'-phosphate ester in the medium, and collecting the nucleoside 5'-phosphate ester from the medium.

(2) The method for producing nucleoside 5'-phosphate ester according to (1), wherein mutations are introduced into the ushA gene and the aphA gene or these genes are disrupted so that they do not function normally.

(3) The method for producing nucleoside 5'-phosphate ester according to (1) or (2), wherein the nucleoside 5'-phosphate ester is selected from the group consisting of 5'-inosinic acid or 5'-guanylic acid.

(4) A *bacterium* belonging to the genus *Escherichia* having an ability to produce nucleoside 5'-phosphate ester, in which ushA gene and aphA gene are disrupted.

(5) The *bacterium* belonging to the genus *Escherichia* according to (4), wherein the nucleoside 5'-phosphate ester is selected from the group consisting of 5'-inosinic acid or 5'-guanylic acid.

(6) A method for searching for a 5'-nucleotidase gene affecting accumulation of nucleoside 5'-phosphate ester, comprising the steps of culturing a parent strain of microorganism and a derivative strain thereof in which a known 5'-nucleotidase is deleted in a minimal medium containing a first nucleoside 5'-phosphate ester as a sole carbon source and a minimal medium containing a second nucleoside 5'-phosphate ester as a sole carbon source to examine expression profiles of genes in the parent strain and the derivative strain, calculating a product of a ratio of expression amounts of each gene in the parent strain and the derivative strain when they are cultured in a medium containing the first nucleoside 5'-phosphate ester as a carbon source and a ratio of expression amounts of each gene in the parent strain and the derivative strain when they are cultured in a medium containing the second nucleoside 5'-phosphate ester as a carbon source, and selecting one or more genes showing a larger value of the product.

(7) The method for searching for a 5'-nucleotidase gene according to (6), wherein the first and second nucleoside 5'-phosphate esters are 5'-inosinic acid and 5'-guanylic acid.

(8) The method for searching for a 5'-nucleotidase gene according to (6) or (7), further comprising the step of selecting a gene that can code for a signal sequence required for transition of a protein into periplasm from the selected genes.

According to the present invention, nucleoside 5'-phosphate ester such as IMP and GMP can be produced by direct fermentation using a *bacterium* belonging to the genus *Escherichia*.

PREFERRED EMBODIMENTS OF THE INVENTION

Hereafter, the present invention will be explained in detail.

<1> Search of an Unknown 5'-nucleotidase Gene

As a known 5'-nucleotidase of *Escherichia coli*, UDP-sugar hydrolase (UshA), which is a product of the ushA gene (GenBank accession X03895), is known. It has been known that the enzyme has 5'-nucleotidase activity that catalyzes dephosphorylation of nucleoside 5'-phosphate such as AMP, GMP, IMP and XMP to produce a corresponding nucleoside (H. C. Neu, (1967) *Journal of Biological Chemistry*, 242, 3896-3904; A. Cowman, I. R. Beacham, (1980) *Gene*, 12, 281-286).

The inventors of the present invention disrupted the ushA gene of *Escherichia coli* W3110 strain, and examined its influence on the nucleotide decomposing ability. The 5'-nucleotidase activity in periplasm of the ushA gene-disrupted W3110 strain (WΔushA) was markedly reduced compared with the W3110 strain. However, when growth of the WΔushA strain was investigated in a minimal medium containing nucleoside-5'-phosphate as a sole carbon source, this strain could grow. Therefore, it was considered that the nucleotide decomposing ability is not completely lost by the disruption of only ushA. Furthermore, when nucleoside-5'-phosphate was used as a sole carbon source, start of the growth was retarded. Therefore, it was expected that there existed another 5'-nucleotidase that was induced when UshA did not function.

The inventor of the present invention attempted to search for an unknown 5'-nucleotidase gene based on the aforementioned findings, and found that a product of a gene reported as an acid phosphatase gene (aphA)(M. C. Thaller, S. Schippa, A. Bonci, S. Cresti, G. M. Rossolini, (1997) *FEMS Microbilogy Letters*, 146, 191-198, GenBank accession X86971) or yjbP (GenBank accession AAC77025) had the 5'-nucleotidase activity.

A gene coding for such a 5'-nucleotidase that affects the accumulation of nucleoside 5'-phosphate as described above can be searched for as follows.

First, a microbial parent strain and a derivative strain thereof in which a known 5'-nucleotidase is deleted are cultured in a minimal medium containing a first nucleoside 5'-phosphate ester or a second nucleoside 5'-phosphate ester such as IMP or GMP as a sole carbon source. When the microorganism is *Escherichia coli*, the known 5'-nucleotidase may be the aforementioned UshA.

Subsequently, gene expression profiles of these strains are investigated. Specifically, a ratio of expression amounts in the wild strain and the derivative strain is investigated for each gene.

Then, a product of a ratio of expression amounts of a gene in the parent strain and the derivative strain when they are cultured in a medium containing the first nucleoside 5'-phosphate as a carbon source and a ratio of expression amounts of the gene in the parent strain and the derivative strain when they are cultured in a medium containing the second nucleoside 5'-phosphate as a carbon source is calculated for each gene, and one or more genes showing a larger value of the product are selected.

Although the method for gene expression profiling is not particularly limited, the DNA array method (H. Tao, C. Bausch, C. Richmond, F. R. Blattner, T. Conway, (1999) *Journal of Bacteriology*, 181, 6425-6440) can be mentioned, for example.

From the aforementioned selected genes, target genes can be further narrowed down by selecting genes that may code a signal sequence required for transition of protein to periplasm. This is because it is expected that the target 5'-nucleotidase transits to periplasm and function therein.

As for *Escherichia coli*, as shown in the examples mentioned later, two kinds of genes, b0220 (also referred to as o157) and yjbP, were selected. Among these genes, yjbP was an acid phosphatase gene (aphA). On the other hand, b0220 was a gene of which function was unidentified, which was designated as ykfE. When these genes were amplified in *Escherichia coli*, remarkable increase of 5'-nucleotidase activity was not observed in the ykfE gene-amplified strain, whereas remarkable increase of 5'-nucleotidase activity was observed in the aphA gene-amplified strain. Thus, it was confirmed that the aphA gene product (AphA) had the 5'-nucleotidase activity. In this way, aphA was found as a gene coding for 5'-nucleotidase that affected the accumulation of nucleoside 5'-phosphate.

<2> *Bacterium* Belonging to the Genus *Escherichia* of the Present Invention The *Bacterium* belonging to the genus *Escherichia* of the present invention is a *bacterium* belonging to the genus *Escherichia* having an ability to produce nucleoside 5'-phosphate, in which the ushA gene and the aphA gene do not function normally. The *Bacterium* belonging to the genus *Escherichia* itself is not particularly limited so long as it is a microorganism belonging to the genus *Escherichia* such as *Escherichia coli*. However, specifically, those mentioned in the reference of Neidhardt et al. (Neidhardt, F. C. et al., *Escherichia coli* and *Salmonella Typhimurium*, American Society for Microbiology, Washington D.C., 1208, Table 1) can be used.

The Bacterium belonging to the genus *Escherichia* of the present invention can be obtained by, for example, breeding a mutant strain or genetic recombinant strain in which the ushA gene and the aphA gene do not normally function using a Bacterium belonging to the genus *Escherichia* having purine nucleoside producing ability as a parent strain. Further, the Bacterium belonging to the genus *Escherichia* of the present invention can also be obtained by breeding similar to the breeding of purine nucleoside producing strain using a strain in which the ushA gene and the aphA gene do not normally function as a parent strain.

Examples of bacteria belonging to the genus *Escherichia* having purine nucleoside producing ability include bacteria belonging to the genus *Escherichia* having an ability to produce inosine, guanosine, adenosine, xanthosine, purine riboside, 6-methoxypurine riboside, 2,6-diaminopurine riboside, 6-fluoropurine riboside, 6-thiopurine riboside, 2-amino-6-thiopurine riboside, mercaptoguanosine or the like. By breeding a mutant strain or genetic recombinant strain in which the ushA gene and the aphA gene do not normally function using these *Escherichia bacteria* having purine nucleoside producing ability as a parent strain, *bacteria* belonging to the genus *Escherichia* having an ability to produce nucleoside 5'-phosphate ester corresponding to each purine nucleoside can be obtained.

The purine nucleoside producing ability referred to in the present invention means an ability to produce and accumulate a purine nucleoside in a medium. Further, the expression of "having purine nucleoside producing ability" means that the microorganism belonging to the genus *Escherichia* produces and accumulates a purine nucleoside in a medium in an amount larger than that obtained with a wild strain of *E. coli*, for example, the W3110 strain.

Further, the ability to produce nucleoside 5'-phosphate ester means an ability to produce and accumulate nucleoside 5'-phosphate ester in a medium. Furthermore, the expression of "having purine nucleoside producing ability" means that the microorganism belonging to the genus *Escherichia* produces and accumulates a purine nucleoside in a medium in an amount larger than that obtained with a wild strain of *E. coli*, for example, the W3110 strain, and it preferably means that the microorganism produces and accumulates nucleoside 5'-phosphate ester in an amount of 100 mg/L or more, more preferably 500 mg/L or more, further preferably 1000 mg/L or more, when it is cultured under the conditions mentioned in Example 6 described later.

*Bacteria* belonging to the genus *Escherichia* having purine nucleoside producing ability are detailed in International Patent Publication WO99/03988, for example. More specifically, there can be mentioned the *Escherichia coli* FADRaddG-8-3::KQ strain (purFKQ, purA$^-$, deoD$^-$, purR$^-$, add$^-$, gsk$^-$) described in the above international patent publication. This strain harbors a mutant purF coding for PRPP amidotransferase of which feedback inhibition by AMP and GMP is desensityzed, and in which the lysine residue at a position of 326 is replaced with a glutamine residue, and a succinyl-AMP synthase gene (purA), purine nucleoside phosphorylase gene (deoD), purine repressor gene (purR), adenosine deaminase gene (add), and inosine/guanosine kinase gene (gsk) are disrupted. This strain given with a private number of AJ13334 was deposited on Jun. 24, 1997 at the National Institute of Bioscience and Human-Technology, Agency of Industrial Science and Technology, Ministry of International Trade and Industry (currently, the independent administrative corporation, National Institute of Advanced Industrial Science and Technology, International Patent Organism Depositary)(Chuo Dai-6, 1-1 Higashi 1-Chome, Tsukuba-shi, Ibaraki-ken, Japan, postal code: 305-5466) as an international deposit under the provisions of the Budapest treaty, and received an accession number of FERM BP-5993. This strain has an ability to produce inosine and guanosine. Further, the strain obtained by introducing a plasmid containing a mutant purF gene into the FADRaddeddyicPpgixapA strain, which was constructed as described in the Example to be mentioned later, can also be suitably used as an inosine producing *bacterium*. Guanosine producing ability can be enhanced by introducing the guaA and guaB genes that encode IMP dehydrogenase and GMP synthetase, respectively, into an inosine producing *bacterium*. In the present invention, the bacterial strain is not limited to the aforementioned strains, and any strains having purine nucleoside producing ability can be used without any particular limitation.

A mutant strain or genetic recombinant strain in which the ushA gene and the aphA gene do not function normally can be obtained by modifying the genes so that the activities of 5'-nucleotidases that are the products of the genes should be decreased or deleted, or transcription of these genes should be decreased or eliminated. Such a microorganism can be obtained by, for example, replacing the ushA gene and the aphA gene on the chromosome with an ushA gene and aphA gene that do not function normally (also referred to as "disrupted ushA gene" and "disrupted aphA gene" hereinafter) by homologous recombination utilizing a genetic recombination method (Experiments in Molecular Genetics, Cold Spring Harbor Laboratory press (1972); Matsuyama, S. and Mizushima, S., *J. Bacteriol.*, 162, 1196 (1985)).

In homologous recombination, a plasmid or the like having a sequence showing homology to a sequence on a chromosome is introduced into a bacterial cell. Then, recombination occurs at a certain frequency at a position of the homologous sequence so that the whole introduced plasmid is incorporated into the chromosome. When recombination is further caused thereafter at the position of the homologous sequence, the plasmid is again removed from the chromosome. At this time, depending on the position of the recombination, the disrupted gene may remain on the chromosome, and the original normal gene may be removed together with the plasmid. By selecting such a bacterial strain, a strain in which the normal ushA gene or aphA gene on the chromosome is replaced with the disrupted ushA gene or the disrupted aphA gene can be obtained.

A gene disruption technique based on such homologous recombination has already been established, and a method utilizing a linear DNA, a method utilizing a temperature sensitive plasmid and so forth can be used. The disruption of the ushA gene and the aphA gene can also be performed by using a plasmid containing an ushA gene or aphA gene internally inserted with a marker gene such as a drug resistance gene, which cannot replicate in a target microbial cell. That is, in a transformant that was transformed with the aforementioned plasmid and hence acquired drug resistance, the marker gene is incorporated into the chromosomal DNA. Since it is highly probable that this marker gene is incorporated into the chromosome by homologous recombination of the ushA gene or aphA gene sequences located on the both ends of the marker gene with those genes on the chromosome, a gene-disrupted strain can be selected efficiently.

The disrupted ushA gene and the disrupted aphA gene used for the gene disruption can be obtained by, specifically, deleting a certain region of these genes by digestion with a restriction enzyme and ligation, inserting another DNA fragment (marker gene etc.) into these genes, or introducing substitution, deletion, insertion, addition or inversion of one or more nucleotides into a nucleotide sequence of coding region, promoter region or the like of the ushA gene or the aphA gene by the site-specific mutagenesis (Kramer, W. and Frits, H. J., *Methods in Enzymology*, 154, 350 (1987)) or treatment with a chemical agent such as sodium hyposulfite or hydroxylamine (Shortle, D. and Nathans, D., *Proc. Natl. Acad. Sci. U.S.A.*, 75, 270 (1978)) so that activity of the encoded repressor should be decreased or deleted, or transcription of the ushA gene or the aphA gene should be decreased or eliminated. Among these embodiments, the method of deleting a certain region of the ushA gene or aphA by digestion with a restriction enzyme and ligation and the method of inserting another DNA fragment into these genes are preferred in view of certainty and stability of the methods. The order of the gene disruption of the ushA gene and the aphA gene is not particularly limited, and either one may be disrupted first.

The nucleotide sequences of the ushA gene and the aphA genes themselves are known, and hence they can be easily obtained by PCR or hybridization based on such nucleotide sequences. For example, the ushA gene can be obtained from chromosome DNA of *Escherichia coli* by PCR using the primers shown in SEQ ID NOS: 1 and 2, for example. Further, the N-terminal region of the aphA gene can be obtained by PCR using the primers shown in SEQ ID NOS: 3 and 7, and the C-terminal region of the same can be obtained by PCR using the primers shown in SEQ ID NOS: 4 and 8.

Whether the target gene has been disrupted or not can be confirmed by analyzing the gene on a chromosome by Southern blotting or PCR.

<3> Method for Producing Nucleoside 5'-phosphate Ester

Nucleoside 5'-phosphate ester can be produced by culturing a bacterium belonging to the genus *Escherichia* having an ability to produce nucleoside 5'-phosphate ester, in which the ushA gene and the aphA gene do not function normally, in a medium to produce and accumulate nucleoside 5'-phosphate ester in the medium, and collecting the nucleoside 5'-phosphate ester from the medium.

The medium may be a usual medium containing a carbon source, nitrogen source, inorganic ions, and other organic components, if needed. As the carbon source, there can be used saccharides such as glucose, lactose, galactose, fructose, arabinose, maltose, xylose, trehalose, ribose and starch hydrolysate, alcohols such as glycerol, mannitol and sorbitol, organic acids such as gluconic acid, fumaric acid, citric acid and succinic acid and so forth.

As the nitrogen source, there can be used inorganic ammonium salts such as ammonium sulfate, ammonium chloride, and ammonium phosphate, organic nitrogen such as soybean hydrolysate, ammonia gas, aqueous ammonia and so forth.

As the organic trace nutrients, it is desirable to add required substances including vitamins such as vitamin B1, nucleic acids such as adenine and RNA or yeast extract in a suitable amount. In addition to these, a small amount of potassium phosphate, magnesium sulfate, iron ions, manganese ions and so forth are added as required.

Culture is preferably carried out under an aerobic condition for 16-72 hours. The culture temperature is controlled to be 30° C. to 45° C., and pH is controlled to be 5 to 8 during the culture. Inorganic or organic, acidic or alkaline substances as well as ammonia gas and so forth can be used for pH adjustment.

Collection of nucleoside 5'-phosphate ester from fermented liquor is usually carried out by a combination of an ion exchange resin method, a precipitation method and other known techniques.

BEST MODE FOR CARRYING OUT THE INVENTION

The present invention will be further specifically explained hereinafter with reference to the following examples.

EXAMPLE 1

Effect of ushA Disruption on Nucleotide Production of *Escherichia coli*

<1> Construction of ushA-Disrupted Strain

From genomic DNA of the *Escherichia coli* W3110 strain, a ushA gene fragment was amplified by PCR. The genomic DNA was extracted by using RNA/DNA maxi Kit (produced by Qiagen). PCR was performed by using the primers shown in SEQ ID NOS: 1 and 2 and Pyrobest DNA Polymerase (produced by Takara Shuzo) according to the instruction appended to the polymerase. After PCR, the amplified DNA fragments were purified by using Wizard PCR Preps (produced by Promega). After digestion with restriction enzymes SphI and SalI (produced by Takara Shuzo), the purified DNA fragments were subjected to a phenol/chloroform treatment and ethanol precipitation. pHSG397 (produced by Takara Shuzo) similarly digested with SphI and SalI was ligated by using DNA ligation Kit Ver.2 (produced by Takara Shuzo).

Competent cells of JM109 (produced by Takara Shuzo) were transformed with the above ligation mixture, and plated on an LB agar plate containing 30 μg/mL of chloramphenicol (produced by Sigma)(LB+chloramphenicol plate). After culturing at 37° C. overnight, grown colonies were cultured in LB medium containing 30 μg/mL of chloramphenicol at 37° C. in a test tube, and a plasmid was extracted using an automatic plasmid extractor, PI-50 (produced by Kurabo Industries). The obtained plasmid was designated as pHSGushA.

Then, an HpaI fragment was removed from the ushA gene contained in pHSGushA as follows. pHSGushA was digested with a restriction enzyme HpaI (produced by Takara Shuzo), subjected to a phenol/chloroform treatment and ethanol precipitation, and ligated by using DNA Ligation Kit Ver.2. JM109 was transformed with this ligation solution, and a plasmid was extracted from emerged colonies. The obtained plasmid was digested with SphI and SalI, and subjected to agarose gel electrophoresis to select a plasmid containing an inserted target fragment in which the HpaI digestion fragment was deleted from the ushA gene region.

The obtained plasmid fragment and a fragment obtained by digesting the temperature sensitive plasmid pMAN997 described in International Patent Publication WO99/03988 with SphI and SalI were ligated. JM109 was transformed with the ligation solution, and colonies were selected at 30° C. on an LB agar plate containing 50 μg/mL of ampicillin (produced by Meiji Seika Kaisha)(LB+ampicillin plate). The colonies were cultured in LB medium containing 50 μg/mL of ampicillin at 30° C. in a test tube, and plasmids were extracted. A plasmid from which a fragment of a desired length could be obtained by digestion with SphI and SalI was used as a plasmid for ushA disruption, pMANΔushA. The above pMAN997 was obtained by exchanging VspI-HindIII fragments of pMAN031 (*J. Bacteriol.*, 162, 1196 (1985)) and pUC19 (produced by Takara Shuzo).

The W3110 strain was transformed with pMANΔushA, and colonies were selected on an LB+ampicillin plate at 30° C. The selected clones were cultured at 30° C. overnight as liquid culture. The culture broth was diluted $10^{-3}$ times, and inoculated on an LB+ampicillin plate, and colonies were selected at 42° C. The selected clones were applied and spread on an LB+ampicillin plate, and cultured at 30° C. Then, ⅛ of the cells on the plate were suspended in 2 mL of LB medium, and cultured at 42° C. for 4 to 5 hours with shaking. The cells diluted $10^{-5}$ times were seeded on an LB plate, and several hundreds of colonies among the obtained colonies were inoculated on an LB plate and LB+ampicillin plate, and growth was confirmed to select ampicillin sensitive strains. Colony PCR was performed for several strains among the ampicillin sensitive strains to confirm the deletion of ushA gene. In this way, an ushA-disrupted strain derived from *E. coli* W3110, WΔushA, was obtained.

<2> Measurement of 5'-nucleotidase and Nucleotide Assimilation Culture

W3110 and WΔushA were cultured at 37° C. in LB medium, and periplasm was extracted from cells in a proliferation phase according to the method of Edwards et al. (C. J. Edwards, D. J. Innes, D. M. Burns, I. R. Beacham, (1993) *FEMS Microbiology Letters*, 114, 293-298). By using the procedure described in the above reference, 5'-nucleotidase activity of periplasmic proteins for IMP, GMP and AMP was measured. Activity producing 1 μmol of phosphoric acid per minute was defined as 1 unit. As a result, the periplasmic 5'-nucleotidase activity of WΔushA was markedly decreased compared with W3110 as shown in Table 1.

TABLE 1

| | Periplasmic 5'-nucleotidase activity (Unit/mg of protein) | | |
|---|---|---|---|
| | Substrate | | |
| Strain | IMP | GMP | AMP |
| W3110 | 14.0 | 10.8 | 14.2 |
| WΔushA | 0.21 | 0.16 | 0.03 |

In order to confirm whether WΔushA had completely lost the nucleotide decomposition ability, its growth was investigated in a minimal medium containing a nucleotide as a sole carbon source. W3110 and WΔushA were cultured overnight at 37° C. in LB medium, then washed with physiological saline, added to 50 mL of M9 minimal medium (J. H. Miller, "A SHORT COURSE IN BACTERIAL GENETICS", Cold Spring Harbor Laboratory Press, New York, 1992) containing 5.8 g/L of IMP or 6.7 g/L of GMP, and cultured at 37° C. After a suitable time had passed, the culture broth was collected and its absorbance at 600 nm was measured by using a spectrophotometer DU640 (produced by Beckman). Although the growth of WΔushA degraded in M9 medium containing IMP or GMP as a carbon source, it could grow in such a medium. This suggested that the nucleotide degradative ability was not completely lost by the disruption of only ushA. Further, since the start of growth was retarded, existence of another 5'-nucleotidase was expected, which was induced when UshA did not function.

EXAMPLE 2

Search of Novel 5'-nucleotidase Gene

It was considered that the 5'-nucleotidase gene predicted in Example 1 was more strongly expressed in WΔushA compared with W3110 when they were cultured in M9 medium containing IMP or GMP as a carbon source. In order to identify the 5'-nucleotidase considered to function in WΔushA, gene expression profiles of W3110 and WΔushA cultured in M9 medium containing IMP or GMP as a carbon source were compared.

For comparison of gene expression profiles, the DNA array method (H. Tao, C. Bausch, C. Richmond, F. R. Blattner, T. Conway, (1999) *Journal of Bacteriology*, 181, 6425-6440) was used. Panorama *E. coli* Gene Arrays (produced by Sigma Genosis) is a DNA array composed of a nylon membrane spotted with amplified DNA fragment of 4290 genes of *E. coli*, and mRNA expression amounts of the total genes of *E. coli* can be comprehensively analyzed at once by using it.

W3110 and WΔushA were cultured in M9 medium containing IMP or GMP as a sole carbon source, and RNA was extracted from the cells at a proliferation phase by using RNeasy mini Kit (produced by Qiagen). The extracted RNA solution was added with $MgCl_2$ and DNaseI (Boeringer Mannheim) at final concentrations of 10 mM and 0.25 U/ml, respectively, to decompose contaminated genomic DNA, and the total RNA were then purified by phenol/chloroform extraction and ethanol precipitation. A reverse transcription reaction was performed by using AMV reverse transcriptase (produced by Promega), dATP, dGTP, dTTP, [$\alpha$-$^{33}$P]-dCTP (all produced by Amersham Pharmacia), and random primer pd(N)$_6$ (produced by Amersham Pharmacia) according to the instructions appended to Panorama *E. coli* Gene Arrays to prepare a cDNA probe. The obtained cDNA probe was purified by using ProbeQuant (produced by Amersham Pharmacia).

By using the cDNA probe obtained above, hybridization and washing were performed according to the instruction appended to Panorama *E. coli* Gene Arrays. The membrane was enclosed in a hybridization bag, and brought into contact with an imaging plate (produced by Fuji Photo Film) for 48 hours, and an image was captured by using FLA3000G (produced by Fuji Photo Film). Concentration of each spot was quantified by using image analysis software, AIS (produced by Imaging Research), and ratio of each spot concentration with respect to the sum of the total spot concentrations on the same membrane was represented for every membrane. Increase and decrease of gene expression was investigated by comparing values of this ratio for each gene.

In this way, genes of which expression amount were larger in WΔushA compared with W3110 when they were cultured in M9 medium containing IMP as a carbon source, and genes of which expression amount were larger in WΔushA compared with W3110 when they were cultured in M9 medium containing GMP as a carbon source were selected, respectively. However, since the change of the carbon source for the culture might cause variation of expression amounts of many genes, the number of selected genes was large, and it was difficult to confirm function of each gene. Therefore, as means for narrowing down the candidate genes, the following screening method was employed.

Since it was considered that the target 5'-nucleotidase gene showed increased expression amount in both of the cultures utilizing IMP and GMP as the carbon source, a product of a ratio of expression amounts in WΔushA and W3110 (WΔushA/W3110) obtained when they were cultured with IMP as the carbon source and a ratio of expression amounts in WΔushA and W3110 (WΔushA/W3110) obtained when they were cultured with GMP as the carbon source was calculated, and a gene showing a large value for the product was searched for. The genes that showed larger values of top 50 are shown in Table 2 (1-25th places) and Table 3 (26-50th places). Among these, genes of which functions were unknown were selected as candidates that might have the 5'-nucleotidase activity. Since WΔushA could grow by decomposing extracellular nucleotides, it was expected that the target 5'-nucleotidase should migrate to periplasm and function therein. Therefore, from those genes of which functions were unknown, only those having a signal sequence required for transition of protein to periplasm were selected. By these screenings, the candidate genes were narrowed down to two kinds, b0220 (or o157) and yjbP.

When these genes were investigated, it was found that b0220 was a gene reported as a gene of unidentified function designated as ykfE, and yjbP was a gene reported as an acid phosphatase gene (aphA)(M. C. Thaller, S. Schippa, A. Bonci, S. Cresti, G. M. Rossolini, (1997) *FEMS Micorobilogy Letters*, 146, 191-198).

TABLE 2

Gene expression profiles observed in
W3110 and WΔushA when they were
cultured in M9 medium containing
IMP or GMP as carbon source
(1-25th places)

| IMP expression Ratio (I) | GMP expression ratio (G) | I × G | Gene |
|---|---|---|---|
| 11.3 | 5.5 | 61.7 | pyrB |
| 3.5 | 7.3 | 25.2 | malE |
| 4.5 | 2.0 | 9.1 | pyrI |
| 3.6 | 2.2 | 8.0 | udp |
| 3.9 | 2.0 | 7.9 | deoD |
| 2.8 | 2.6 | 7.2 | yeiN |
| 1.9 | 3.7 | 7.2 | lamB |
| 5.1 | 1.2 | 6.0 | b0220 (o157) |
| 3.5 | 1.7 | 5.9 | DeoA |
| 2.1 | 2.7 | 5.5 | YeiC |
| 2.1 | 2.6 | 5.4 | tsx |
| 3.0 | 1.8 | 5.3 | b1036 (o173) |
| 4.2 | 1.2 | 4.9 | DeoC |
| 2.3 | 2.1 | 4.8 | NupC |
| 2.4 | 2.0 | 4.8 | FadB |
| 2.1 | 2.3 | 4.8 | YejD |
| 1.5 | 3.2 | 4.8 | MalF |
| 1.9 | 2.3 | 4.4 | CirA |
| 2.6 | 1.7 | 4.3 | CarA |
| 1.5 | 2.9 | 4.2 | LivJ |
| 3.2 | 1.3 | 4.0 | TalB |
| 0.9 | 4.5 | 4.0 | FliD |
| 1.5 | 2.6 | 4.0 | MalM |
| 1.6 | 2.4 | 3.9 | DppA |
| 1.0 | 4.0 | 3.8 | FliC |

TABLE 3

Gene expression profiles observed in
W3110 and WΔushA when they were
cultured in M9 medium containing
IMP or GMP as carbon source
(26-50th places)

| IMP expression Ratio (I) | GMP expression Ratio (G) | I × G | Gene |
|---|---|---|---|
| 0.8 | 4.4 | 3.7 | CheA |
| 2.8 | 1.3 | 3.7 | DeoB |
| 1.3 | 2.7 | 3.6 | GlpK |
| 2.1 | 1.7 | 3.5 | b2341 (f714) |
| 1.8 | 1.8 | 3.3 | YeiK |
| 2.8 | 1.2 | 3.3 | Cdd |
| 2.0 | 1.6 | 3.2 | b2673 (o81) |
| 1.8 | 1.7 | 3.1 | YeiP |
| 1.9 | 1.7 | 3.1 | YeiR |
| 0.9 | 3.3 | 3.0 | MotB |
| 3.1 | 1.0 | 3.0 | YafP |
| 2.0 | 1.5 | 3.0 | b0221 (f826) |
| 1.6 | 1.8 | 2.9 | yjbP |
| 0.7 | 4.0 | 2.9 | tap |
| 1.9 | 1.5 | 2.9 | pyrH |
| 1.5 | 1.9 | 2.8 | sseA |
| 1.8 | 1.6 | 2.8 | ybeK |
| 0.8 | 3.3 | 2.7 | flgN |
| 1.9 | 1.4 | 2.7 | glnA |
| 2.0 | 1.3 | 2.7 | ygaD |
| 2.3 | 1.2 | 2.7 | entE |
| 1.7 | 1.6 | 2.6 | yafY |
| 1.9 | 1.4 | 2.6 | nupG |
| 1.8 | 1.7 | 2.6 | fepA |
| 1.2 | 2.2 | 2.6 | b3524 (hypothetical) |

EXAMPLE 3

Evaluation of Candidate Genes by Gene Amplification

Strains in which the candidate genes obtained in Example 2, ykfE and aphA, were each amplified were prepared to investigate the influence of the gene amplification on the 5'-nucleotidase activity. The gene fragments of ykfE and aphA were amplified by using the primers shown in SEQ ID NOS: 3 and 4, and the primers shown in SEQ ID NOS: 5 and 6, respectively. The ykfE fragment was cloned into a vector pSTV28 (produced by Takara Shuzo) at a cleavage site obtained with restriction enzymes SalI and PstI (produced by Takara Shuzo) to obtain pSTVykfE. Further, the aphA fragment was cloned into pSTV28 at a cleavage site obtained with SalI and SphI to obtain pSTVaphA. WΔushA was transformed with each of the plasmids prepared as described above, and cultured at 37° C. in LB medium containing 30 μg/mL of chloramphenicol. The 5'-nucleotidase activity for IMP, GMP and AMP as a substrate in periplasm of cells in a proliferation phase was measured. As a result, the aphA gene amplification provided marked increase of the 5'-nucleotidase activity compared with a strain harboring only the vector as shown in Table 4, and thus it was confirmed that the AphA protein had the activity. On the other hand, the ykfE-amplified strain did not show significant increase of the activity, and thus it was determined that it did not have the 5'-nucleotidase activity.

TABLE 4

5'-Nucleotidase activity in
periplasm of aphA- and ykfE-amplified strains
(U/mg of protein)

| Strain | Substrate | | |
|---|---|---|---|
|  | IMP | GMP | AMP |
| WΔushA/pSTV | 0.074 | 0.067 | 0.024 |
| WΔushA/pSTVykfE | 0.15 | 0.15 | 0.067 |
| WΔushA/pSTVaphA | 3.2 | 3.5 | 1.8 |

EXAMPLE 4

Introduction of aphA Disruption into WΔushA

Gene disruption was performed in WΔushA strain for aphA, which was expected to be a gene for the 5'-nucleotidase activity. A fragment of the N-terminus region and fragment of the C-terminus region of aphA were amplified by PCR using the primers shown in SEQ ID NOS: 3 and 7 and the primers shown in SEQ ID NOS: 4 and 8, respectively, and purified by using Wizard PCR Preps. The amplification reaction solutions in an amount of 1 μL each were mixed, added to a PCR reaction solution and subjected to crossover PCR (A. J. Link, D. Phillips, G. M. Church (1997) *Journal of Bacteriology*, 179, 6228-6237) using the primers shown in SEQ ID NOS: 3 and 4 to obtain an aphA gene fragment including deletion of its center portion of about 300 nucleotides. This fragment was inserted into an SalI-SphI cleavage site of temperature sensitive plasmid pMAN997 to obtain a plasmid pMANΔaphA for gene disruption. By using this plasmid for gene disruption, each aphA of W3110 and WΔushA was disrupted to obtain an aphA-deficient strain (WΔaphA) and ushA- and aphA-double deficient strain (WΔushAΔaphA).

EXAMPLE 5

Measurement of 5'-nucleotidase Activity and Nucleotide Assimilation Culture of WΔushAΔaphA W3110, WΔushA, WΔaphA and WΔushAΔaphA were each cultured at 37° C. in LB medium, and 5'-nucleotidase activity in periplasm of cells in a proliferation phase was measured. The results are shown in Table 5. Although the activity in WΔaphA was reduced about by half compared with W3110, it still strongly remained, and it was considered that ushA contributed to it. On the other hand, the 5'-nucleotidase activity in the periplasm of WΔushAΔaphA, which was a double-deficient strain, was further reduced and substantially eliminated.

TABLE 5

5'-Nucleotidase activity of W3110, WΔushA, WΔaphA, and WΔushAΔaphA (U/mg of protein)

| Strain | Substrate | | | |
|---|---|---|---|---|
| | IMP | GMP | AMP | XMP |
| W3110 | 14.0 | 10.9 | 14.2 | 8.7 |
| WΔaphA | 5.8 | 4.1 | 6.0 | 3.9 |
| WΔushA | 0.21 | 0.16 | 0.03 | 0.10 |
| WΔushAΔaphA | 0.010 | 0.009 | 0.012 | 0.019 |

Furthermore, in order to investigate the nucleotide degradative ability of each strain, these strains were cultured in M9 medium containing IMP or GMP as a carbon source in flasks. While growth was observed for W3110, WΔaphA and WΔushA with both of the carbon sources with growth intensities in that order, growth was not observed for WΔushAΔaphA even though it was cultured for 300 hours, and thus it was revealed that it could not grow in M9 medium containing IMP or GMP as a sole carbon source. In this way, the ability to decompose extracellular nucleotide of $E.$ $coli$ W3110 was successfully deleted by double deficiency of ushA and aphA.

EXAMPLE 6

Gene Disruption for ushA and aphA in Inosine Producing Bacterium

In order to investigate the possibility of direct fermentation of IMP, the gene disruption was performed for ushA and aphA in an inosine producing strain of $Escherichia$ $coli$. As the inosine producing $bacterium$, FADRaddeddyicPpgixapA (referred to as "I" hereinafter) described in International Patent Publication WO99/03988 was used. The mutant purF gene fragment contained in the plasmid pKFpurFKQ mentioned in WO99/03988 was digested with BamHI and HindIII, then purified and ligated to pMW218 (produced by Nippon Gene) digested with the same enzymes. The obtained plasmid pMWpurFKQ was introduced into the I strain. The obtained strain, I/pMWpurFKQ, became a strain having ability to accumulate about 2-3 g/L of inosine in culture broth.

The aforementioned strain FADRaddeddyicPpgixapA was a strain in which PRPP amidotransferase gene (purF), succinyl-AMP synthase gene (purA), purine nucleoside phosphorylase gene (deoD), purine repressor gene (purR), adenosine deaminase gene (add), 6-phosphogluconate dehydrase gene (edd), adenine deaminase gene (yicP), phosphoglucose isomerase gene (pgi) and xanthosine phosphorylase gene (xapA) were disrupted. Further, pKFpurFKQ contained a mutant purF coding for PRPP amidotransferase in which the 326th lysine residue was replaced with a glutamine residue, and of which feedback inhibition by AMP and GMP was canceled (see International Patent Publication WO99/03988).

By using the aforementioned plasmid pMANΔushA for ushA gene disruption and the plasmid pMANΔaphA for aphA gene disruption, a ushA-single deficient strain (IΔushA/pMWpurFKQ), aphA-single deficient strain (IΔaphA/pMWpurFKQ) and ushA- and aphA-double deficient strain (IΔushAΔaphA/pMWpurFKQ) were obtained.

Each of the aforementioned strains was evaluated for IMP producing ability. Medium, culture methods and analysis method for the evaluation of IMP producing ability are shown below.

[Base medium: MS medium]

| | Final concentration |
|---|---|
| Glucose | 40 g/L (separately sterilized) |
| (NH$_4$)$_2$SO$_4$ | 16 g/L |
| KH$_2$PO$_4$ | 1 g/L |
| MgSO$_4$ 7H$_2$O | 1 g/L |
| FeSO$_4$ 7H$_2$O | 0.01 g/L |
| MnSO$_4$ 4H$_2$O | 0.01 g/L |
| Yeast extract | 8 g/L |
| CaCO$_3$ | 30 g/L (separately sterilized) |

[Culture Method]

Refresh culture: stored cells were inoculated, LB agar medium (added with necessary agents), 37° C., overnight.

Seed culture: refreshed cells were inoculated, LB broth (added with necessary agents), 37° C., overnight.

Main culture: seed culture broth was inoculated in an amount of 2%, MS medium (added with adenine and other agents as required), 37° C., 20 ml, in 500-ml volume Sakaguchi flask.

[Analysis Method]

In an amount of 500 μl of the culture broth was sampled in a time course, and centrifuged at 15,000 rpm for 5 minutes, and the supernatant was diluted 4 times with H$_2$O and analyzed by HPLC.

Analysis Conditions:
Column: Asahipak GS-220 (7.6 mm ID×500 mm L)
Buffer: 0.2 M NaH$_4$PO$_4$ (adjusted to pH 3.98 with phosphoric acid)
Temperature: 55° C.
Flow rate: 1.5 ml/min
Detection: UV 254 nm
Retention time (min)

| | |
|---|---|
| Inosine | 16.40 |
| IMP | 11.50 |
| Guanosine | 19.67 |
| GMP | 13.04 |

The results are shown in Table 6. In Table 6, results of two parallel experiments are indicated, respectively. It was demonstrated that IΔushAΔaphA accumulated about 1.0 g/L at most of IMP in the culture broth.

TABLE 6

Evaluation of ushA- and aphA-deficient strains of inosine producing bacterium by culture in flask

| Strain | Culture time (h) | Inosine (g/L) | IMP (g/L) |
|---|---|---|---|
| I/pMWpurFKQ | 48 | 2.3 | 0 |
|  | 48 | 2.3 | 0 |
| IΔushA/pMWpurFKQ | 51 | 3.1 | 0 |
|  | 51 | 2.9 | 0 |
| IΔaphA/pMWpurFKQ | 51 | 3.6 | 0 |
|  | 51 | 3.2 | 0 |
| IΔushAΔaphA/pMWpurFKQ | 54 | 2.4 | 1.0 |
|  | 54 | 2.6 | 0.6 |

EXAMPLE 7

Production of GMP by ushA- and aphA-double Deficient Strain

In order to examine the possibility of GMP production by the present invention, guanosine producing ability was imparted to the ushA- and aphA-double deficient strain obtained in Example 6, IΔushAΔaphA/pMWpurFKQ. Impartation or enhancement of guanosine producing ability was attained by enhancing genes of enzymes catalyzing reactions from IMP to GMP. The reaction converting IMP to XMP is catalyzed by IMP dehydrogenase encoded by guaA, and the reaction converting XMP to GMP is catalyzed by GMP synthetase encoded by guaB, and it is known that these genes constitute an operon (guaBA) in *Escherichia coli*. Therefore, PCR was performed by using the primer shown in SEQ ID NOS: 9 and 10 to amplify guaBA operon of *Escherichia coli*. The amplified fragment was purified, and the restriction enzyme sites formed on the both ends were digested with SacI and KpnI. The digested fragment was ligated to pSTV28 similarly digested with SacI and KpnI, and a plasmid pSTVguaBA into which the guaBA gene was incorporated was selected. This plasmid can coexist with the plasmid pMWpurFKQ harbored by IΔushAΔaphA/pMWpurFKQ.

The aforementioned pSTVguaBA was introduced into the IΔushAΔaphA/pMWpurFKQ strain to obtain IΔushAΔaphA/pMWpurFKQ/pSTVguaBA strain. Further, as a control, IΔushAΔaphA/pMWpurFKQ/pSTV28 strain was prepared, which was introduced with the vector pSTV28.

According to the same culture methods and analysis method as in Example 6, inosine, IMP, guanosine and GMP accumulated in the culture broth were quantified for the IΔushAΔaphA/pMWpurFKQ/pSTVguaBA strain and IΔushAΔaphA/pMWpurFKQ/pSTV28 strain. The results are shown in Table 7. In the IΔushAΔaphA/pMWpurFKQ/pSTV28 strain used as a control, the culture time was prolonged due to the influence of the introduction of pSTV28, and it provided a result different from that of the IΔushAΔaphA/pMWpurFKQ/pSTVguaBA strain. Guanosine could not be quantified, since its peaks overlapped with other peaks. On the other hand, it was demonstrated that the IΔushAΔaphA/pMWpurFKQ/pSTVguaBA strain accumulated about 0.1 g/L of GMP in the culture broth thanks to the introduction of guaBA.

TABLE 7

Culture of ushA- and aphA-deficient strain of inosine producing bacteria in flask

| Strain | Culture time (h) | Inosine (g/L) | IMP (g/L) | Guanosine (g/L) | GMP (g/L) |
|---|---|---|---|---|---|
| IΔushAΔaphA/pMWpurFKQ/pSTV2B | 78 | 9.7 | 0.4 | —* | 0.0 |
| IΔushAΔaphA/PMWpurFKQ/PSTVguaBA | 78 | 3.4 | 0.2 | 1.1 | 0.1 |

*indicates that quantification was not possible.

What is claimed is:

1. A method for producing nucleoside 5'-phosphate ester, comprising the steps of culturing a bacterium belonging to *Escherichia coli* having an ability to produce nucleoside 5'-phosphate ester, in which expression of ushA gene and aphA gene is decreased as compared to a wild type strain by mutating or disrupting the ushA gene and the aphA gene, in a medium to produce and accumulate nucleoside 5'-phosphate ester in a medium, and collecting the nucleoside 5'-phosphate ester from the medium, wherein the nucleoside 5'-phosphate ester is selected from the group consisting of inosine 5'-phosphate ester and guanosine 5'-phosphate ester, and wherein the 5'-nucleotidase activity in the periplasm is substantially eliminated.

2. The method according to claim 1, wherein the bacterium is further transformed with the mutant purF gene of *Escherichia coli* coding for PRPP amidotransferase in which the lysine residue at position 326 is replaced with a glutamine residue.

3. The method according to claim 2, wherein the bacterium is further transformed with a guaBA operon of *Escherichia coil*.

4. The method according to claim 1, wherein the nucleoside 5'-phosphate ester is inosine 5'-phosphate ester.

5. The method according to claim 1, wherein the nucleoside 5'-phosphate ester is guanosine 5'-phosphate ester.

* * * * *

UNITED STATES PATENT AND TRADEMARK OFFICE
CERTIFICATE OF CORRECTION

PATENT NO.      : 7,575,901 B2             Page 1 of 1
APPLICATION NO. : 10/798339
DATED           : August 18, 2009
INVENTOR(S)     : Kakehi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 964 days.

Signed and Sealed this

Seventh Day of September, 2010

David J. Kappos
*Director of the United States Patent and Trademark Office*

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Synthetic DNA

<400> SEQUENCE: 1
cgcgcatgct cgtcgctttg ggttttc    27

<210> SEQ ID NO 2
<211> LENGTH: 27
<212> TYPE: DNA
<213> ORGANISM: Artificial Sequence
<220> FEATURE:
<223> OTHER INFORMATION: Synthetic DNA

<400> SEQUENCE: 2
cgcgtcgacc acgatccggc tgaaacc    27

```
<210> SEQ ID NO 3
<211> LENGTH: 27
<212> TYPE: DNA
<213> ORGANISM: Artificial Sequence
<220> FEATURE:
<223> OTHER INFORMATION: Synthetic DNA

<400> SEQUENCE: 3
cccgtcgaca ctgctgcgcc ttagctg                                         27

<210> SEQ ID NO 4
<211> LENGTH: 27
<212> TYPE: DNA
<213> ORGANISM: Artificial Sequence
<220> FEATURE:
<223> OTHER INFORMATION: Synthetic DNA

<400> SEQUENCE: 4
cccctgcagg cagtattaac gttgatg                                         27

<210> SEQ ID NO 5
<211> LENGTH: 27
<212> TYPE: DNA
<213> ORGANISM: Artificial Sequence
<220> FEATURE:
<223> OTHER INFORMATION: Synthetic DNA

<400> SEQUENCE: 5
cgcgtcgaca tcaccattgt agggtag                                         27

<210> SEQ ID NO 6
<211> LENGTH: 27
<212> TYPE: DNA
<213> ORGANISM: Artificial Sequence
<220> FEATURE:
<223> OTHER INFORMATION: Synthetic DNA

<400> SEQUENCE: 6
cgcgcatgcc agcaagacag cgaaagg                                         27

<210> SEQ ID NO 7
<211> LENGTH: 36
<212> TYPE: DNA
<213> ORGANISM: Artificial Sequence
<220> FEATURE:
<223> OTHER INFORMATION: Synthetic DNA

<400> SEQUENCE: 7
gcatatcaat cagctggccg aacaataagc aaacgg                               36

<210> SEQ ID NO 8
<211> LENGTH: 18
<212> TYPE: DNA
<213> ORGANISM: Artificial Sequence
<220> FEATURE:
<223> OTHER INFORMATION: Synthetic DNA

<400> SEQUENCE: 8
gccagctgat tgatatgc                                                   18

<210> SEQ ID NO 9
<211> LENGTH: 27
<212> TYPE: DNA
<213> ORGANISM: Artificial Sequence
<220> FEATURE:
<223> OTHER INFORMATION: Synthetic DNA
```

```
<400> SEQUENCE: 9
cgcgagctca ttcagtcgat agtaacc                                          27

<210> SEQ ID NO 10
<211> LENGTH: 27
<212> TYPE: DNA
<213> ORGANISM: Artificial Sequence
<220> FEATURE:
<223> OTHER INFORMATION: Synthetic DNA

<400> SEQUENCE: 10
gccggtacct caatcctata attcttg                                          27
```